(12) United States Patent
Ripart et al.

(10) Patent No.: US 6,493,582 B1
(45) Date of Patent: Dec. 10, 2002

(54) PROGRAMMABLE MULTISITE CARDIAC PACING DEVICE AND METHOD

(75) Inventors: Alain Ripart, Gif sur Yvette (FR); Renzo Dal Mlion, Chatillon (FR)

(73) Assignee: Ela Medical S.A., Montrouge (FR)

( * ) Notice: Subject to any disclaimer, the term of this patent is extended or adjusted under 35 U.S.C. 154(b) by 242 days.

(21) Appl. No.: 09/181,363

(22) Filed: Oct. 28, 1998

(30) Foreign Application Priority Data

Oct. 19, 1997 (FR) .............................................. 97 13493

(51) Int. Cl.[7] .............................................. A61N 1/762
(52) U.S. Cl. .......................................................... 607/9
(58) Field of Search ...................................... 607/9, 36

(56) References Cited

U.S. PATENT DOCUMENTS

| 4,549,548 A | | 10/1985 | Wittkampf et al. | |
|---|---|---|---|---|
| 4,928,688 A | | 5/1990 | Mower | |
| 5,403,356 A | | 4/1995 | Hill et al. | |
| 5,439,482 A | | 8/1995 | Adams et al. | |
| 5,514,161 A | * | 5/1996 | Limousin | ...................... 607/9 |
| 5,646,586 A | * | 7/1997 | Meltzer | ...................... 607/116 |
| 5,720,768 A | * | 2/1998 | Verboven-Nelissen | ......... 607/9 |
| 5,814,090 A | * | 9/1998 | Latterell et al. | ............... 607/36 |

FOREIGN PATENT DOCUMENTS

| EP | 0676217 | 10/1995 |
|---|---|---|
| WO | WO 98/09680 | 3/1998 |

* cited by examiner

Primary Examiner—George R. Evanisko
(74) Attorney, Agent, or Firm—Orrick, Herrington & Sutcliffe LLP

(57) ABSTRACT

In the "multisite" pacing device of the present invention, electrodes are placed in a plurality of respective distinct sites including at least one ventricular site (22, 24). These electrodes are connected to a circuit for cardiac signal collection to detect a depolarization potential at the corresponding site, as well as to a stimulation circuit (30) to apply necessary stimulation impulses at this same site. The stimulation circuit, common to the electrodes, is selectively and programmably connected to and one and/or the other of the right and/or left electrodes of the concerned cavity. The stimulation circuit can particularly be a circuit programmable in either a bipolar or monopolar stimulation mode, where the selection means applies the stimulation impulse to one of the electrodes when the circuit is programmed in monopolar mode, and to the two electrodes when the circuit is programmed in bipolar mode.

14 Claims, 1 Drawing Sheet

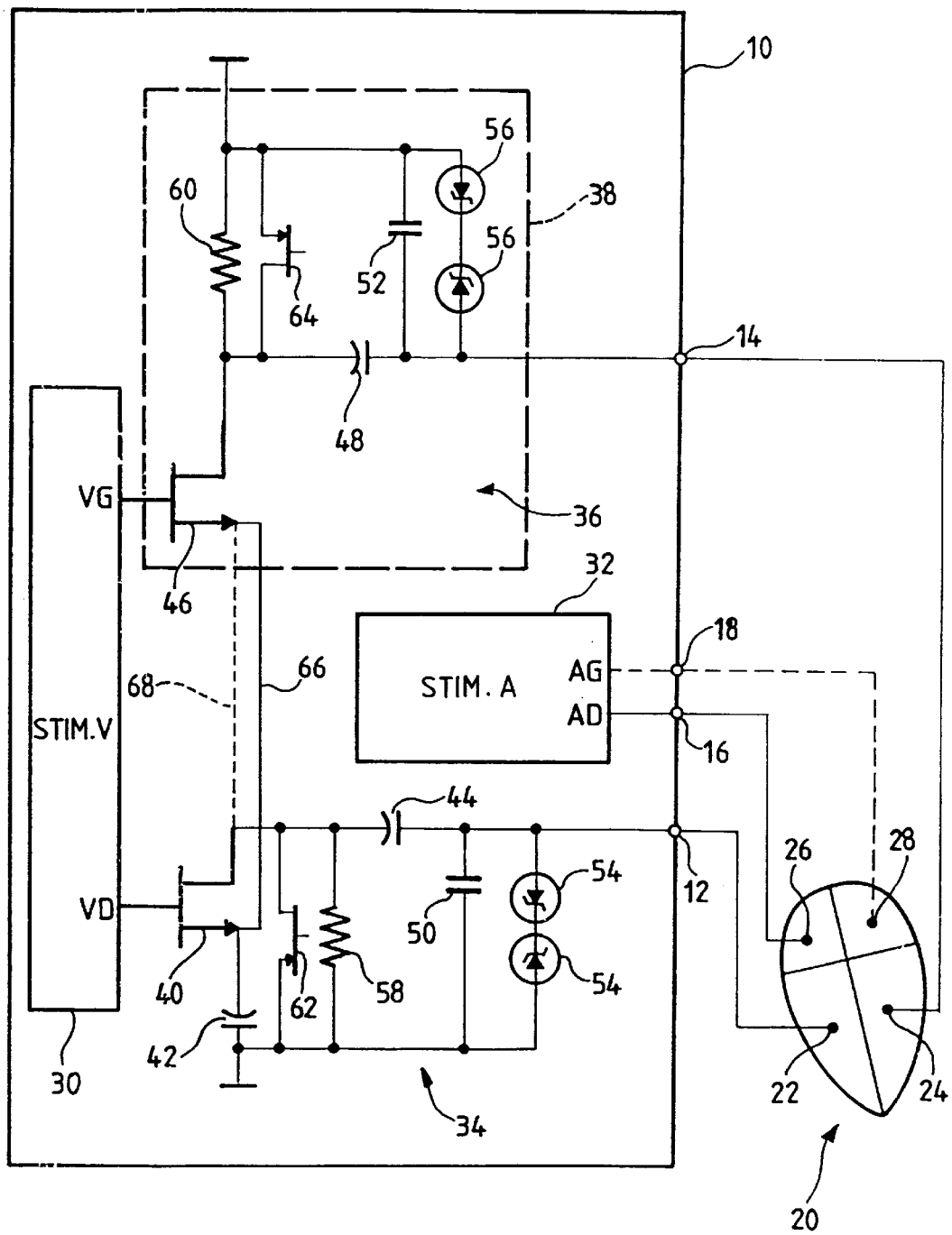

PROGRAMMABLE MULTISITE CARDIAC PACING DEVICE AND METHOD

FIELD OF THE INVENTION

The present invention is related to cardiac pacemakers and stimulation circuits of a defibrillator or cardiovertor, and more particularly to their utilization for the treatment of cardiac insufficiency by stimulation.

BACKGROUND OF THE INVENTION

In addition to treating irregularities of the cardiac rhythm by stimulation, it is also known to so treat irregularities of myocardial contraction observed in patients with cardiac insufficiency, whether spontaneous or induced by a traditional stimulation. A study by J. C. Daubert et al., *Stimucaur*, Volume 25, no 3, pp. 170–176 surveys works on this subject.

"Multisite" pacemakers are known for stimulating the right and left cavities of the heart. In these multisite pacemakers, electrodes are placed in a plurality of respective distinct sites of the heart, including at least one ventricular site. These devices can provide double ventricular stimulation, double ventricular stimulation with right atrial stimulation (so called "triple chamber" models) or double ventricular stimulation with double atrial stimulation (so called "quadruple chamber" models).

In double ventricular treatments, the stimulation of the two ventricular sites must be simultaneous. This is typically accomplished by use of a classic pacemaker comprising a bipolar connector for ventricular stimulation, to which a particular probe comprising a <<Y>> adapter is connected where one end of the adapter (i.e., the bottom of the <<Y>>) allows a bipolar (i.e., two conductor) connection to the connector of the pacemaker, and the other end (i.e., each of branches of the <<Y>>) allows a connection of two unipolar probes, each corresponding to one of the two respective conductors of the bipolar part and ending at the two ventricular sites, right and left. Such a configuration allows transformation of the bipolar output of a classic pacemaker into two simultaneous unipolar outputs.

Nevertheless, the utilization of such a <<Y>> connector is not without its disadvantages—both at the moment of implantation, since it is necessary to put in place and to safely lodge the connector, and later (in terms of reliability), particularly due to the difficulty of maintaining a perfect seal against organic fluids surrounding the connector.

Furthermore this assembly, once put in place, systematically produces double stimulation (of the two ventricular sites), without it being possible later (after implantation) to suppress one stimulation, for example, following the elevation of threshold on one of the probes, except of course by a new intervention.

OBJECTS AND SUMMARY OF THE INVENTION

One of the objects of the present invention is to overcome these various disadvantages by allowing double simultaneous stimulation of two ventricular sites (and/or two atrial sites) with no intermediate <<Y>> connector, thereby avoiding all the attendant difficulties of this particular adapter.

Another object of the present invention is to provide a device that can individually command either one or the other, or both, stimulations, for example, by selectively programming either double ventricular stimulation, stimulation of the right ventricle alone or stimulation of the left ventricle alone, the selection being implementable and operable in a non-invasive manner and by means of a known device such as a programmer associated with the pacemaker, for example, via telemetry.

A further object is implementation of the present invention in preexisting models of classic pacemakers, for example, the Chorum™ series of products available from the assignee hereof, Ela Medical, with modification necessary only to the output stage by incorporation of an additional circuit, avoiding redesign of the main circuit of the pacemaker or the control software thereof.

More preferably, the pacing device of the present invention is a pacemaker of the aforementioned "multisite" type where electrodes are placed in a plurality of respective distinct sites including at least one ventricular site and are connected to a cardiac signal collection circuit for detecting a depolarization potential at the corresponding site, and to a stimulation circuit for applying, when necessary, a stimulation impulse to the same site, characterized in that the pacemaker comprises programmable selection means to selectively connect the stimulation circuit that is common to them, and either one and/or the other of the right and/or left electrodes of the particular cavity.

In an alternative embodiment of the present invention, each of the electrodes possesses a connector with the selection means disposed between the stimulation circuit and the respective connectors of the electrodes.

In a further alternative embodiment, a stimulation impulse can be simultaneously applied on these two electrodes when the selection means select and consequently connect the two electrodes, right and left, to the stimulation circuit.

In another embodiment, the configuration of the selection means can be defined by a programmer temporarily coupled to the pacemaker, for example, by telemetry.

In yet another embodiment, the plurality of respective distinct sites includes at least one ventricular site and two atrial sites, distinct ventricular stimulation means and atrial stimulation means are provided, and the selection means is programmable to selectively connect one and/or the other of the right, and/or the left, ventricular electrodes to the ventricular stimulation circuit, and to selectively connect one and/or the other of the right and/or left atrial electrodes to the atrial stimulation circuit.

In another alternative embodiment, the additional components of the selection means are mounted on a flexible circuit connected to the main circuit of the pacemaker which also supports the components of the stimulation circuit.

Preferably, the stimulation circuit is a programmable circuit, which is programmable in either a monopolar or bipolar stimulation mode, where the selection means causes application of the stimulation impulse to one of the electrodes when the circuit is programmed in monopolar mode, and to two electrodes when the circuit is programmed in bipolar mode.

BRIEF DESCRIPTION OF THE DRAWING

Further features, characteristics and advantages of the invention will be understood by those persons of ordinary skill in the art in view of the following detailed description of a preferred embodiment of the present invention, made with reference to the annexed drawing, which illustrates one embodiment of a multisite cardiac pacing device according to the present invention.

DETAILED DESCRIPTION OF THE DRAWING

In the FIGURE, circuit 10 of a "quadruple chamber" type cardiac pacemaker is shown where four monopolar outputs 12, 14, 16, 18 are connected by one or several appropriate probes (cardiac leads) to the myocardium 20 at respective distinct sites 22 (right ventricle), 24 (left ventricle), 26 (right atrium) and 28 (left atrium).

Circuit 10 includes a ventricular stimulation circuit ("STIM.V") 30 with two outputs VD and VG for the respective stimulation of the right 22 and left 24 ventricle, and an atrial stimulation circuit ("STIM.A") 32 with two outputs AD and AG for the respective stimulation of the right 26 and left 28 atrium.

In an alternative implementation, the pacemaker can be of the "triple chamber" type where only one of the atria, preferably the right atrium, is stimulated.

In another variant, the stimulation can be limited to the ventricles obviating the need for the atrial stimulation circuit 32.

The multisite cardiac pacemaker of the present invention further comprises known circuits of detection of ventricular and atrial cardiac signals, which will not be described in detail to the extent that the invention concerns the stimulation aspect for treating irregularities of the cardiac rhythm.

The ventricular stimulation circuit 30 can be an unmodified circuit of a conventional device, particularly a ventricular stimulation circuit programmable in a bipolar mode (for example, that of the Chorum™ series of pacemaker), where the control software of the pacemaker allows a therapist to choose either monopolar (signal present on only one of the two poles) or bipolar (signal present on both of the two poles) stimulation modes.

The two outputs of this circuit correspond then, in the framework of the invention, to designated outputs VD and VG in FIG. 1.

Similarly, the atrial stimulation circuit 32, if implemented, will operate in the same manner as the ventricular stimulation circuit 30 and with the corresponding additional components that will be described below with respect to the ventricular stimulation circuit 30. Therefore description of more detail specifically concerning the atrial stimulation circuit 32 will not be included.

The output VD is connected to circuit 34 that controls the probe mounted on connector 12, and the output VG is connected to a circuit 36 that controls the probe mounted on the connector 14.

Circuit 34 can be the output stage of a known classic pacemaker, which will need only slight modification for implementation of the present invention.

Circuit 36 is constituted from a small number of additional components that can be mounted, in this embodiment, on a flexible circuit 38 attached to the main preexisting circuit supporting all components of the pacemaker.

To stimulate the right ventricle, a signal VD is delivered by circuit 30, rendering transistor 40 active (i.e., turning it "on" to render it conductive), allowing a transfer of charge from capacitor 42, mounted between the source of transistor 40 and ground and charged beforehand to an appropriate potential, to capacitor 44, mounted between the drain of transistor 40 and output 12 to which the probe extending to the site 22 of stimulation of the right ventricle is connected.

To stimulate the left ventricle, a signal VG is delivered by circuit 30, rendering transistor 46 active, allowing a transfer of charge from capacitor 42, charged beforehand to an appropriate potential, to capacitor 48, mounted between the drain of transistor 46 and output 14 to which the probe extending to the site 24 of stimulation of the left ventricle is connected.

To stimulate both the left and the right ventricle, circuit 30 delivers signals VD and VG that render both transistors 40 and 46 active, thus transferring the charge of the aforementioned capacitor 42 to both the aforementioned capacitor 44 and the aforementioned capacitor 48. In order to obtain balanced charge transfer, the capacitance of each of capacitors 44 and 48 is on the order of half of that of capacitor 42.

Various auxiliary circuits and features can be incorporated in alternative embodiments, including:

- capacitors 50 and 52 for electromagnetic interference filtering, mounted between outputs 12 and 14 respectively and ground;
- Zener diodes 54,54 and 56,56 mounted in opposition between respective outputs 12 and 14 and ground, for limiting unwanted potentials from being induced due to extraneous perturbations on probes connecting these outputs to the myocardium (i.e., high voltage protection);
- resistors 58 and 60 mounted between respective capacitors 44 and 48 and ground, to adjust the discharge profile of the respective capacitor by the choice of an appropriate time constant RC;
- transistors 62 and 64 to allow short-circuiting of resistors 58 and 60 to end discharge after a predetermined duration, programmable by the pacemaker.

With the aforementioned configuration, it is possible to choose either to stimulate simultaneously the left and right ventricle in unipolar mode when circuit 30 is programmed in "bipolar" stimulation mode, or to stimulate only one ventricle, the right or the left, also in unipolar mode, when circuit 30 is programmed in "unipolar" stimulation mode.

Simultaneous stimulation of the left and right ventricle, can be performed either by concurrent commands VG and VD (i.e., where VG and VD are the same), or including the command VD in the command VG (i.e., in others words, command VG is longer and includes the command VD).

The present invention advantageously disposes of the aforementioned disadvantageous choice previously necessitated at the time of implantation and disadvantages encountered later during the service life of the device as discussed above with respect to known devices.

Indeed, if the device is, for example, programmed in "bipolar" mode where there is stimulation of the two (right and left) ventricles, and a progressive elevation of the threshold on the left probe is observed, the device of the present invention can easily be re-programmed in "monopolar" ("unipolar") mode to prevent one stimulation circuit from stimulating and to thereby stimulate only one of the ventricles.

Alternatively, connection 66 between the respective sources of transistors 40 and 46 can be replaced by connection 68 between the source of transistor 46 and the drain of transistor 40, where the resulting configuration allows, by choice, either to simultaneously stimulate the left and the right ventricle in unipolar mode when circuit 30 is programmed in "bipolar" stimulation mode, or to stimulate only the right ventricle alone in unipolar mode when circuit 30 is programmed "unipolar" stimulation mode.

In another alternative embodiment, both conductors 66 and 68 are omitted and a capacitor of similar capacitance as that of capacitor 42 is mounted between the source of transistor 46 and ground (not shown) so as to render the left ventrical stimulation circuit independent of the right stimulation circuit.

Of course, as indicated above, what has been discussed with respect to left and/or right ventricular stimulation is directly applicable to left and/or right atrial stimulation for the implementation of a triple or quadruple chamber pacemaker.

The present invention has been described with reference to specific embodiments thereof. It will be understood by one skilled in the art that these are not exclusive embodiments, and while the foregoing description of illustrative embodiments discusses certain specificities, these enabling details should not be construed as limiting the scope of the invention, and it will be readily understood by those persons skilled in the art that the present invention is susceptible to many modifications, adaptations, and equivalent implementations without departing from this scope and without diminishing its advantages.

We claim:

1. A multisite cardiac pacemaker for pacing selectively at least one of a left and a right cavity of a heart, comprising:
   a cardiac signal collection circuit to detect a depolarization potential;
   at least one stimulation circuit to generate a stimulation pulse and control an application of stimulation pulses;
   a first connector for receiving a first electrode adapted to be placed in at least one ventricular stimulation site, a second connector for receiving a second electrode adapted to be placed in at least one atrial stimulation site, and a third connector for receiving a third electrode adapted to be placed in a cardiac cavity stimulation site, wherein each of said first, second and third connectors passes a depolarization potential received thereat and a stimulation pulse received thereat; and
   programmable selection means for selectively connecting the first, second and third connectors to the stimulation circuit and to the cardiac signal collection circuit, wherein the programmable selection means has a first pacing configuration in which at least one of the first, second and third connectors is connected to said stimulation circuit for unipolar stimulation of said corresponding stimulation site, and a second pacing configuration in which at least two of said first, second and third connectors are connected to said stimulation circuit for simultaneous bipolar stimulation of a left cardiac chamber stimulation site and a right cardiac chamber stimulation site.

2. The pacemaker of claim 1, wherein the configuration of the selection means is adapted to be defined by a programmer coupled temporarily to the pacemaker.

3. The pacemaker of claim 1, wherein the stimulation circuit further comprises a ventricular stimulation circuit and an atrial stimulation circuit, wherein the programmable selection means is programmable to selectively connect the ventricular stimulation circuit to said first connector, and to selectively connect the atrial stimulation circuit to at least one of the second and third connectors.

4. The pacemaker of claim 1, further comprising a flexible circuit board and a main circuit board wherein the programmable selection means is mounted on said flexible circuit, said flexible circuit is connected to the main circuit, and the stimulation circuit is mounted on the main circuit board.

5. The pacemaker of claim 1, wherein the stimulation circuit is a programmable circuit, having a unipolar stimulation mode, wherein the selection means controls application of the stimulation pulse to one of the first and third connectors.

6. The pacemaker of claim 1, wherein the stimulation circuit is a programmable circuit having a bipolar stimulation mode, and wherein the programmable selection means controls application of the stimulation pulses to one of said first and third connectors, wherein the third connector has a corresponding electrode adapted to be placed in a ventricular stimulation site, and wherein the second and third connectors respectively have corresponding electrodes in different atrial stimulation sites.

7. A method for multisite cardiac pacing of the heart, comprising:
   providing at least one stimulation circuit for controlling an application of stimulation pulses;
   selecting a plurality of distinct respective stimulation sites comprising at least one ventricular stimulation site;
   placing at least one electrode in at least one of the plurality of stimulation sites;
   providing a programmable selection means for selectively connecting each of the at least one electrodes to the stimulation circuit in a predetermined pacing configuration;
   programming the programmable selection means to connect selected ones of said electrodes to have one of a first pacing configuration in which the stimulation circuit is operated in a unipolar stimulation mode and a stimulation pulse is delivered to at least one of said electrodes, and a bipolar stimulation mode in which a stimulation pulse is delivered to at least two of said electrodes, said at least two electrodes having corresponding stimulation sites in one of an atrium an a ventricle;
   detecting a depolarization potential at at least one of the distinct stimulation sites; and
   delivering stimulation pulses according to the programmed pacing configuration.

8. The method of claim 7, further comprising placing a first electrode to a left cardiac cavity site and placing a second electrode to a right cardiac cavity site, and wherein programming said programmable selection means further comprises connecting the first electrode and the second electrode to a stimulation means, in a bipolar stimulation mode wherein delivering stimulation pulses further comprises delivering the stimulation pulse simultaneously on the first and second electrodes.

9. The method of claim 8, further comprising defining the pacing configuration of the programmable selection means by temporarily coupling a programmer to the pacemaker.

10. The method of claim 7, wherein the plurality of distinct respective sites further comprises a first atrial site and a second atrial site, wherein providing at least one stimulation circuit further comprises providing a ventricular stimulation circuit and an atrial stimulation circuit, and wherein programming the programmable selection means further comprises connecting at lease one ventricular electrode to the ventricular stimulation circuit, and connecting at least one of the first and second atrial electrodes to the atrial stimulation circuit.

11. The method of claim 10 wherein programming the programmable selection means further comprises connecting each of the first and second atrial electrodes to the atrial stimulation circuit in a bipolar stimulation mode.

12. The method of claim 11 further comprising placing the first atrial electrode in the left atrium and placing the second atrial electrode in the right atrium.

13. The method of claim 11 further comprising providing a second ventricular electrode and wherein programming the programmable selections means further comprises connecting the first and the second ventricular electrodes to the ventricular stimulation circuit in a bipolar stimulation mode.

14. The method of claim 7, further comprising:
   providing a main circuit board;
   mounting the stimulation circuit on the main circuit board;
   providing a flexible circuit board;
   mounting the programmable selection means on the flexible circuit board; and
   connecting the flexible circuit board to the main circuit board.

* * * * *